United States Patent
Al-Ali et al.

(10) Patent No.: US 8,337,403 B2
(45) Date of Patent: Dec. 25, 2012

(54) PATIENT MONITOR HAVING CONTEXT-BASED SENSITIVITY ADJUSTMENTS

(75) Inventors: Ammar Al-Ali, Tustin, CA (US); Massi E. Kiani, Laguna Niguel, CA (US); Walter M. Weber, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 365 days.

(21) Appl. No.: 12/254,748

(22) Filed: Oct. 20, 2008

(65) Prior Publication Data

US 2009/0048495 A1  Feb. 19, 2009

Related U.S. Application Data

(63) Continuation of application No. 11/071,875, filed on Mar. 3, 2005, now Pat. No. 7,438,683.

(60) Provisional application No. 60/549,996, filed on Mar. 4, 2004.

(51) Int. Cl.
*A61B 5/00* (2006.01)

(52) U.S. Cl. .................... 600/300; 600/323; 600/372

(58) Field of Classification Search .......... 600/300–301, 600/309–310, 320–321, 322–328, 344, 353, 600/355, 363, 364, 368, 379, 382, 384, 481, 600/500–505; 128/920–925
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,069,214 A * | 12/1991 | Samaras et al. | 600/323 |
| 5,163,438 A | 11/1992 | Gordon et al. | |
| 5,206,807 A * | 4/1993 | Hatke et al. | 600/484 |
| 5,262,944 A * | 11/1993 | Weisner et al. | 600/300 |
| 5,337,744 A | 8/1994 | Branigan | |
| 5,341,805 A | 8/1994 | Stavridi et al. | |
| 5,348,004 A * | 9/1994 | Hollub | 600/323 |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |

(Continued)

OTHER PUBLICATIONS

Operators Manual for the Nellcor® N-200 Pulse Oximeter (NPL_Nellcor_2003.pdf), p. 1-96.*

(Continued)

*Primary Examiner* — Henry M Johnson, III
*Assistant Examiner* — Marie Archer
(74) *Attorney, Agent, or Firm* — Knobbe, Martens, Olson & Bear LLP

(57) ABSTRACT

An application identification sensor comprises a plurality of emitters configured to transmit light into a tissue site and a detector configured to receive the light after tissue absorption. The detector generates a signal responsive to the intensity of the light and communicates the signal to a monitor. An information element is readable by the monitor so as to identify a sensor application. The monitor presets at least one user-selectable operational parameter in response to the information element.

9 Claims, 1 Drawing Sheet

U.S. PATENT DOCUMENTS

| | | | |
|---|---|---|---|
| 5,456,252 A | 10/1995 | Vari et al. | |
| 5,473,536 A * | 12/1995 | Wimmer | 700/90 |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,918 A * | 1/1999 | Schradi et al. | 600/300 |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,083,156 A * | 7/2000 | Lisiecki | 600/301 |
| 6,088,607 A | 7/2000 | Diab et al. | |
| 6,110,522 A | 8/2000 | Lepper, Jr. et al. | |
| 6,124,597 A | 9/2000 | Shehada et al. | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,421,549 B1 * | 7/2002 | Jacques | 600/331 |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,628,975 B1 * | 9/2003 | Fein et al. | 600/323 |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Diab et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,801,798 B2 * | 10/2004 | Geddes et al. | 600/323 |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |

| | | |
|---|---|---|
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,311,666 B2 * | 12/2007 | Stupp et al. .................. 600/300 |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 2002/0161291 A1 * | 10/2002 | Kianl et al. .................. 600/324 |
| 2004/0204635 A1 * | 10/2004 | Scharf et al. .................. 600/323 |

OTHER PUBLICATIONS

Lie, C. et al, in "Comparison of the Nellcor 200 and N-300 pulse oximeters during simulated postoperative activities", Anesthesia, May 1997, 52(5):450-452 (Abstract), p. 1.*

Malviya, S. et al in "False Alarms and Sensitivity of Conventional Pulse Oximetry Versus the Masimo SET™ Technology in the Pediatric Postanesthesia Care Unit", Anesth Analg 2000;90, p. 1336-1340.*

Rheineck, A. T. et al in "Advanced Pulse Oximeter Signal Processing Technology Compared to Simple Averaging. II. Effect on Frequency of Alarms in the Postanesthesia Care Unit", Journal of Clinical Anesthesia 11, p. 196-200, 1999.*

Rheineck, A. T. et al in "Advanced Pulse Oximeter Signal Processing Technology Compared to Simple Averaging. I. Effect on Frequency of Alarms in the Operating Room", Journal of Clinical Anesthesia 11:192-195, 1999.*

NPL_Pulse_Oximetry_study.pdf, p. 1-28.*

* cited by examiner

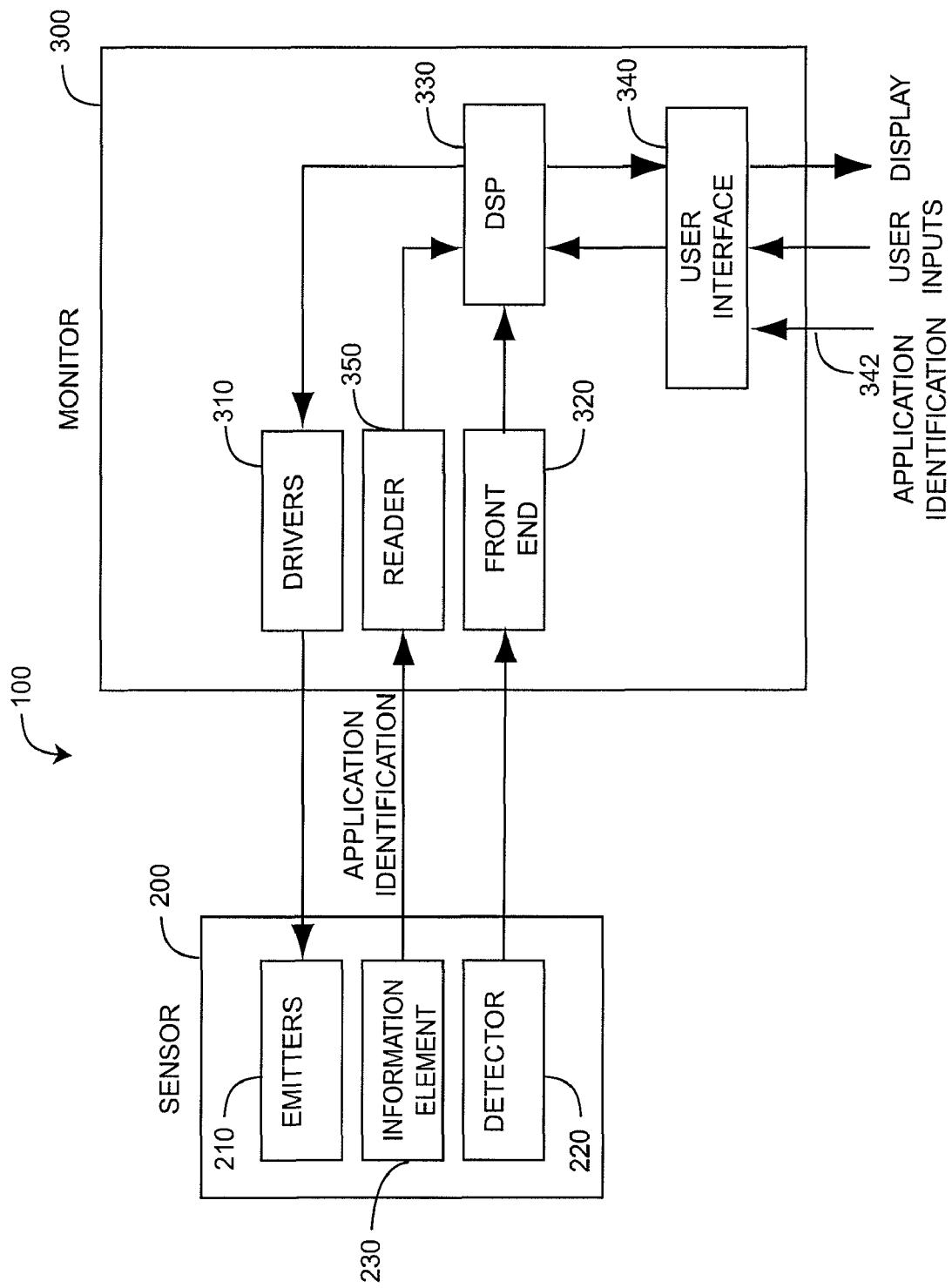

PATIENT MONITOR HAVING CONTEXT-BASED SENSITIVITY ADJUSTMENTS

CROSS-REFERENCE TO RELATED APPLICATIONS

This application is a continuation of U.S. patent application Ser. No. 11/071,875, entitled "Application Identification Sensor," filed Mar. 3, 2005, which will issue as U.S. Pat. No. 7,438,683 on Oct. 21, 2008, which, claims a priority benefit under 35 U.S.C. §119(e) from U.S. Provisional Patent Application No. 60/549,996, entitled "Application Identification Sensor," filed Mar. 4, 2004. The present application incorporates the entirety of the aforementioned priority documents herein by reference.

BACKGROUND OF THE INVENTION

Pulse oximetry is a widely accepted noninvasive procedure for measuring the oxygen saturation level of arterial blood, an indicator of a person's oxygen supply. A typical pulse oximetry system has a sensor, a monitor and a patient cable providing a communication path between the sensor and monitor. The sensor is adapted to attach to a tissue site, such as a patient's finger, and respond to hemaglobin constituents of pulsatile blood. The monitor is adapted to receive a physiological signal from the sensor and provide a numeric readout of the patient's oxygen saturation and pulse rate.

SUMMARY OF THE INVENTION

A conventional pulse oximetry monitor processes the physiological signal from the sensor based upon sensor calibration data, internal algorithm parameters and user-selectable operational parameters. The sensor may have an information element that is readable by the monitor and that identifies one or more characteristics of the sensor. These characteristics may relate to sensor components, such as emitter wavelength, or the sensor type, such as adult, pediatric or neo-natal. The monitor may select calibration data and internal parameters accordingly. An information element may be a passive device, such as a resistor, or an active device, such as a transistor network, a logic device or a memory chip. An information element is described in U.S. Pat. No. 5,758,644 entitled Manual and Automatic Probe Calibration, which is assigned to Masimo Corporation, Irvine, Calif. and incorporated by reference herein.

One aspect of an application identification sensor comprises a plurality of emitters configured to transmit light into a tissue site and a detector configured to receive the light after tissue absorption. The detector generates a signal responsive to the intensity of the light and communicates the signal to a monitor. An information element is readable by the monitor so as to identify a sensor application. The monitor presets at least one user-selectable operational parameter in response to the information element. In one embodiment, the application relates to emergency care and the user-selectable operational parameter is selected from the set of sensitivity and averaging time.

Another aspect of an application identification sensor is a method where a sensor is attached to a monitor and an information element is read. Data from the information element is associated with an application, and user-selectable parameters corresponding to the application are preset. In one embodiment, the application is identified as emergency related. In a particular embodiment, maximum sensitivity and minimum averaging time are selected for processing a signal from the sensor.

An aspect of an application identification apparatus comprises a sensor configured to generate a physiological signal and a monitor capable of processing the physiological signal so as to measure a physiological parameter responsive to a constituent of pulsatile blood. The monitor has an application identification input. User-selectable operational parameters for said monitor have values responsive to the application identification input. In one embodiment, the application identification input is provided by an information element associated with the sensor and readable by the monitor. In another embodiment, the application identification input is provided by a user-actuated button associated with the monitor.

BRIEF DESCRIPTION OF THE DRAWINGS

FIG. 1 is a block diagram a pulse oximetry system utilizing an application identification sensor or an application identification user input or both.

DETAILED DESCRIPTION OF THE PREFERRED EMBODIMENTS

FIG. 1 illustrates a pulse oximetry system 100 incorporating an application identification sensor 200 and a monitor 300 adapted to recognize the sensor 200 accordingly. The sensor 200 has emitters 210 adapted to transmit light into a tissue site and a detector 220 adapted to receive light after absorption by the tissue site and to generate a detector signal in response, as is well known in the art. The monitor 300 has drivers 310 that activate the emitters 210 and a front-end 320 that conditions and digitizes the detector signal for input into a digital signal processor (DSP) 330, as is also well known in the art. The DSP 330 computes oxygen saturation and pulse rate and provides the results on a display. A user interface 340 allows a user to input selected operational parameters for the DSP 330. A pulse oximeter monitor is described in U.S. Pat. No. 6,699,194 entitled Signal Processing Apparatus and Method and U.S. Pat. No. 6,650,917 entitled Signal Processing Apparatus, which are assigned to Masimo Corporation, Irvine, Calif. and incorporated by reference herein. A user interface is described in U.S. Pat. No. 6,658,276 entitled Pulse Oximeter User Interface, which is assigned to Masimo Corporation, Irvine, Calif. and incorporated by reference herein.

Also shown in FIG. 1, the application identification sensor 200 also has an information element 230, and the monitor has a corresponding information element reader 350. Advantageously, the sensor 200 is manufactured with an information element 230 that identifies a particular application to the monitor 300. The monitor 300 presets one or more user-selectable operational parameters accordingly. This reduces or eliminates the need for user input of operational parameters specific to a particular application. In an alternative embodiment, the monitor 300 has an application identification button, switch or other user-actuated device 342 that causes the monitor 300 to preset one or more user-selectable operational parameters.

In one particularly advantageous embodiment, the application identification sensor 200 is manufactured, packaged and/or labeled for use in a trauma or emergency care situation, and the information element 230 is configured to identify that application or use to the monitor 300 accordingly. For example, when such a sensor 200 is connected to the monitor 300, the monitor 300 may select maximum sensitivity and minimum averaging time, providing hands-off optimum settings for these user-selectable operational parameters for a trauma care application. In an alternative embodiment, the monitor 300 has an application identification button 342 that is labeled for use in trauma or emergency care situations and that, when actuated, causes the monitor 300 to set user-selectable operational parameters accordingly.

For various applications, an application identification sensor 200 may indicate other user-selectable operational parameters relating to monitor alarms, displays, outputs and general characteristics to name a few. Alarm parameters may include alarm limits, delay and volume, for example. Display parameters may regard numeric, plethysmograph and trend formats to name a few. Output parameters may include, for instance, the analog output and alarm output types and digital output data formats. General characteristics may include operational modes such as maximum sensitivity and minimum averaging time cited above. General characteristics may also include averaging mode, such as described in U.S. Pat. No. 6,430,525 entitled Variable Mode Averager, which is assigned to Masimo Corporation, Irvine, Calif. and incorporated by reference herein. General characteristics may further include, for example, user key lock-out and password entry to enable user keys and other monitor functions.

An application identification sensor has been disclosed in detail in connection with various embodiments. These embodiments are disclosed by way of examples only and are not to limit the scope of the claims that follow. For example, although an application identification sensor has been described with respect to a pulse oximetry system, a sensor having an information element that identifies an application to a monitor can be utilized in systems capable of measuring physiological parameters other than or in addition to oxygen saturation and pulse rate. One of ordinary skill in art will appreciate many other variations and modifications.

What is claimed is:

1. A patient monitoring device configurable for differing operational conditions, said device comprising:

a physiological signal input configured to receive a physiological signal from a noninvasive optical sensor, said physiological signal indicative of one or more physiological parameters of a patient being monitored;

a signal processing device configured to process said physiological signal and to determine values of said one or more physiological parameters, said processing of said physiological signal including accessing a plurality of configurable processing parameters, at least some of said configurable processing parameters affecting a sensitivity of said processing to changes in said physiological signal, the patient monitoring device being configurable to operate in a first configuration and a second configuration, wherein said sensitivity is greater in the second configuration than in the first configuration; and a single caregiver-actuated emergency care input that, when actuated a single time, causes the patient monitoring device to operate in the second configuration and electronically adjusts a plurality of said at least some configurable processing parameters to increase said sensitivity for emergency care situations.

2. The patient monitoring device of claim 1, wherein said caregiver-actuated emergency care input comprises an input button.

3. The patient monitoring device of claim 1, wherein said caregiver-actuated emergency care input comprises an input switch.

4. The patient monitoring device of claim 1, wherein upon actuation of said caregiver-actuated emergency care input, said electronic adjustment adjusts said at least some configurable processing parameters to operate in a maximum sensitivity mode.

5. The patient monitoring device of claim 1, wherein upon actuation of said caregiver-actuated emergency care input, said electronic adjustment adjusts said at least some configurable processing parameters to operate in a minimum averaging time mode.

6. A method of configuring a patient monitor based at least in part on an environment of use of said patient monitor, the method comprising:

receiving electronic signals indicative of one or more physiological parameters of a monitored patient, said electronic signals indicative of light attenuated by body tissue of a monitored patient;

receiving a single caregiver input indicative of a current patient monitoring environment, wherein a single actuation of said caregiver input causes a patient monitor to transition between a first configuration and a second configuration, wherein the first second configuration is associated with increased processing sensitivity as compared to the first configuration, and wherein said single actuation electronically adjusts a plurality of configurable processing parameters; and processing with a signal processor said electronic signals according to said caregiver input to determine output measurements for said one or more physiological parameters of said monitored patient, wherein a sensitivity of said processing is responsive to said plurality of configurable processing parameters.

7. The method of claim 6, wherein said current patient monitoring environment comprises a trauma care or emergency environment.

8. The method of claim 6, wherein said current patient monitoring environment comprises a non-emergency environment.

9. The method of claim 6, wherein said actuation of said caregiver input electronically adjusts an averaging time parameter of the signal processor.

\* \* \* \* \*

UNITED STATES PATENT AND TRADEMARK OFFICE
CERTIFICATE OF CORRECTION

Page 1 of 1

PATENT NO. : 8,337,403 B2
APPLICATION NO. : 12/254748
DATED : December 25, 2012
INVENTOR(S) : Al-Ali et al.

It is certified that error appears in the above-identified patent and that said Letters Patent is hereby corrected as shown below:

In the Claims:

In column 4 at line 33, In Claim 6, before "second" delete "first".

Signed and Sealed this
Ninth Day of July, 2013

Teresa Stanek Rea
*Acting Director of the United States Patent and Trademark Office*